United States Patent [19]

Ogawa et al.

[11] Patent Number: 5,427,093
[45] Date of Patent: Jun. 27, 1995

[54] OXIMETER PROBE

[75] Inventors: Keikitsu Ogawa; Hideo Ozawa; Yoshiaki Shindo, all of Tokyo, Japan

[73] Assignee: Nihon Kohden Corporation, Tokyo, Japan

[21] Appl. No.: 126,299

[22] Filed: Sep. 24, 1993

[30] Foreign Application Priority Data

Sep. 25, 1992 [JP] Japan .................. 4-066621 U
Feb. 25, 1993 [JP] Japan .................. 5-07093 U

[51] Int. Cl.⁶ ............................................. A61B 5/00
[52] U.S. Cl. ........................................... 128/633
[58] Field of Search ............... 128/632, 633-635, 128/664, 665; 356/39-41

[56] References Cited

U.S. PATENT DOCUMENTS

| | | | |
|---|---|---|---|
| 4,700,708 | 10/1987 | New, Jr. et al. | 356/41 X |
| 4,830,014 | 5/1989 | Goodman et al. | 128/665 |
| 4,865,038 | 9/1989 | Rich et al. | 356/41 X |
| 4,928,691 | 5/1990 | Nicolson et al. | 128/633 |
| 4,974,591 | 12/1990 | Awazu et al. | 128/633 |
| 5,054,488 | 10/1991 | Muz | 128/633 |
| 5,090,410 | 2/1992 | Saper et al. | 128/633 |
| 5,109,849 | 5/1992 | Goodman et al. | 128/633 |
| 5,170,786 | 12/1992 | Thomas et al. | 128/665 X |
| 5,217,013 | 6/1993 | Lewis et al. | 356/41 X |

*Primary Examiner*—Lee S. Cohen
*Assistant Examiner*—Samuel Gilbert
*Attorney, Agent, or Firm*—Sughure, Mion, Zinn, Macpeak & Seas

[57] ABSTRACT

An object of the present invention is to prevent "low-temperature burn" that occurs on account of heat generation by the LED in an oximeter probe. The oximeter probe comprises adhesive tape which has an opening formed at the site where the LED is fitted, and a heat-dissipating plate is provided in the opening.

3 Claims, 1 Drawing Sheet

OXIMETER PROBE

BACKGROUND OF THE INVENTION

1. Field of the Invention

The present invention relates to an oximeter probe that is to be fitted on the skin of a subject to determine photoelectrically the oxygen saturation of hemoglobin in a sample of blood flowing through the tissue of the skin.

2. Related Art

An oximeter probe of the type contemplated by the present invention comprises typically a sheet of adhesive tape that has a light-emitting diode (LED) as a light-emitting device and a photodiode (PD) as a light-receiving device spaced from each other on the adhesive surface of the tape by a distance of about 10 to 30 mm. When the LED is switched on after the adhesive tape is attached to the skin of a human subject, light from the LED illuminates blood vessels in the skin tissue and the reflected light is received by the PD, with the change in the quantity of light reception being used as a basis for determining the oxygen saturation of a sample of blood flowing through the blood vessels.

A problem with this prior art oximeter probe is that the heat generated by the LED accumulates inside the adhesive tape to potentially cause "low-temperature burn" on the skin of the subject.

SUMMARY OF THE INVENTION

In view of the foregoing problem, it is an object to provide an oximeter probe that attenuates the heat generation by the LED so that the subject will not be shocked by "low-temperature burn".

As one aspect of the present invention, there is provided the oximeter probe comprising an adhesive tape detachably bonded to the skin of a human body, as well as a light-emitting device and a light-receiving device that are spaced from each other on the adhesive surface of the adhesive tape, wherein an opening is formed in said adhesive tape at the site where the light-emitting device is fitted and that a heat-dissipating plate is provided in the opening.

In accordance with another aspect of the present invention, the heat-dissipating plate is provided in said opening in such a way that it covers part or all of the surface of the adhesive tape that is opposite the adhesive surface thereof.

Moreover, in accordance with the present invention, the heat generated by the LED during measurement diffuses through the heat-dissipating plate to be radiated to ambient air, thereby attenuating the temperature elevation on the skin surface of the subject. As a consequence, the subject is protected against the hazard of "low-temperature burn".

DETAILED DESCRIPTION OF THE PREFERRED EMBODIMENT

An oximeter probe according to an embodiment of the present invention will now be described with reference to the accompanying drawings.

Figure 1A:
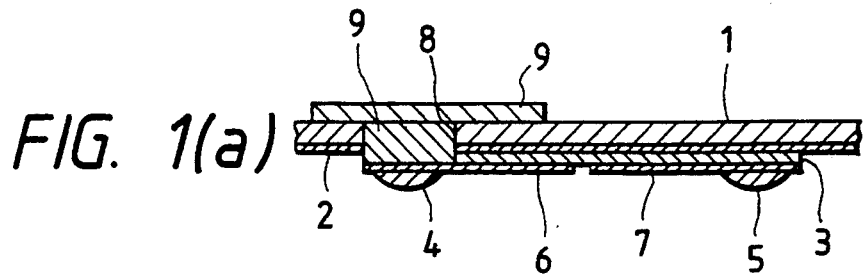
FIGS. 1(a) and (b) are longitudinal sectional views showing diagrammatically an oximeter probe according to an embodiment of the present invention.
Figure 1B:
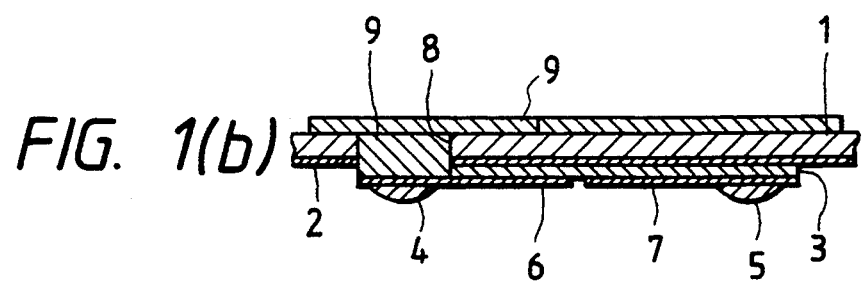
Figure 2:
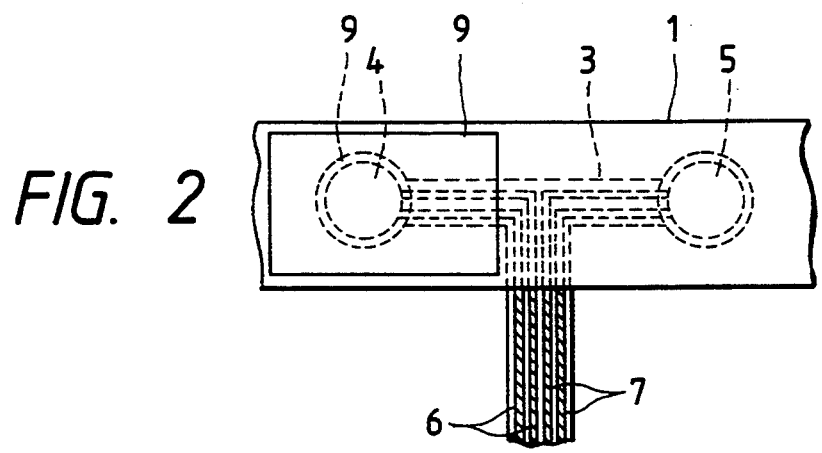
FIG. 2 is a plan view of FIG. 1.

The oximeter probe according to an embodiment of the present invention is shown schematically in FIGS. 1(a), 1(b) and 2. Shown by 1 is a strip of flexible adhesive tape 1 that has an adhesive layer 2 coated on one surface. A generally T-shaped flexible printed-wiring board (PWB) 3 is bonded to the adhesive-coated surface of the tape. An LED 4 and a PD 5 are attached to opposite ends of the PWB 3 in the longitudinal direction of the adhesive tape 1. Wired patterns 6 and 7 formed on the PWB 3 extend out of the adhesive tape 1 at right angles to its length, thereby providing electric leads to the LED 4 and PD 5, respectively.

A generally circular opening 8 is formed through the adhesive tape 1 at the site where the LED 4 is fitted. A heat-dissipating plate 9 formed of a metal or a material having good thermal conductivity such as a silicone resin or a silicone rubber is fitted into the opening 8. The LED 4 and the heat-dissipating plate 9 are thermally connected by means of the PWB 3. The heat-dissipating plate 9 is formed in such a way that it covers at least part of the surface of the adhesive tape 1 that is opposite the surface coated with the adhesive layer 2.

Figure 3:
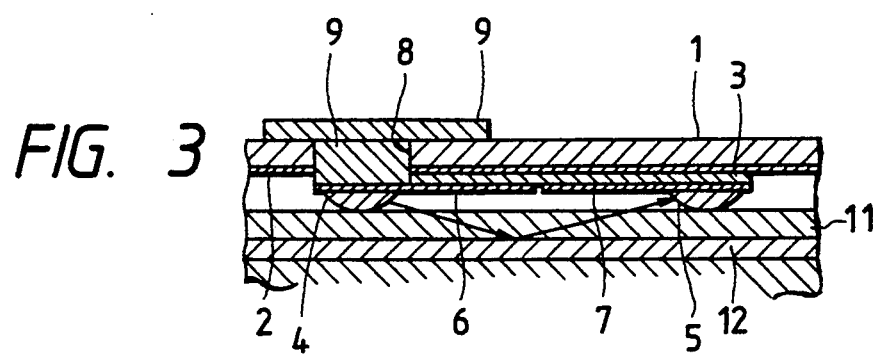
FIG. 3 is a longitudinal sectional view illustrating the operation of the oximeter probe shown in FIG. 1.

The operation of the oximeter probe in accordance with the embodiment under consideration is described below with reference to FIG. 3. The adhesive tape 1 is attached to the skin 11 of a subject with the aid of the adhesive 2 and this brings both the light-emitting face of the LED 4 and the light-receiving face of the PD 5 into contact with the skin 11. When the LED 4 is activated, light is emitted from it and passes through the tissue of the skin 11 to illuminate a blood vessel 12. The light is then reflected by the blood flowing through the blood vessel 12 and the reflected light makes another passage through the tissue of the skin 11 to be launched into the PD 5. The light illuminating the blood is absorbed in a quantity that is related to the oxygen saturation of hemoglobin in the blood, thereby causing a change in the quantity of reflected light. Therefore, if one measures the change in the quantity of reflected light by means of the PD 5, he can determine the content of oxygen in arterial blood.

Any heat that is generated by the LED 4 during measurement diffuses through the heat-dissipating plate 9 to be radiated into ambient air, thereby attenuating the temperature elevation in the area of the skin 11 that contacts the LED 4. As a result, the subject can be protected against "low-temperature burn" due to the accumulation of heat in the oximeter probe, thereby enabling it to determine the oxygen saturation of blood in the correct manner.

As described on the foregoing pages, the oximeter probe of the present invention is so adapted that the heat generated by the LED will be radiated to ambient air by means of the heat-dissipating plate and this enables the oxygen saturation of hemoglobin in a sample of blood to be correctly determined without causing "low-temperature burn" in the subject.

What is claimed is:

1. An oximeter probe comprising:
   an adhesive tape having an adhesive surface and a surface that is opposite to the adhesive surface, the adhesive surface adapted to be bonded to skin of a living body, the adhesive tape having an opening formed therethrough;

a light-emitting device and a light-receiving device spaced from each other on the adhesive surface of the adhesive tape, the light-emitting device being disposed at a location which is aligned with the opening of the adhesive tape; and a heat-dissipating plate being fitted into the opening and being thermally connected to said light-emitting device, wherein the heat dissipating plate covers at least a part of the surface of the adhesive tape that is opposite to the adhesive surface of the adhesive tape.

2. An oximeter probe as claimed in claim 1, wherein the heat dissipating plate is made of one of silicone resin or silicone rubber.

3. An oximeter probe comprising:

an adhesive tape having an adhesive surface and a surface that is opposite to the adhesive surface, the adhesive surface adapted to be bonded to skin of a living body, the adhesive tape having an opening formed therethrough;

a light-emitting device and a light-receiving device spaced from each other on the adhesive surface of the adhesive tape, the light-emitting device being disposed at a location which is aligned with the opening of the adhesive tape;

a heat-dissipating plate being fitted into the opening and being thermally connected to said light-emitting device; and a flexible printed-wiring board which is bonded to the adhesive surface of the adhesive tape, the light-emitting device and the light-receiving device being attached to said flexible printed-wiring board, said light-emitting device and said heat-dissipating plate being thermally connected by said flexible printed-wiring board.

* * * * *